United States Patent [19]
Goodman et al.

[11] Patent Number: 6,093,537
[45] Date of Patent: Jul. 25, 2000

[54] DOUBLE RECEPTOR POLYNUCLEOTIDE ASSAY METHOD

[75] Inventors: Thomas C. Goodman, Mountain View; Edwin F. Ullman, Atherton, both of Calif.

[73] Assignee: Dade Behring Marburg GmbH, Marburg, Germany

[21] Appl. No.: 08/051,512

[22] Filed: Apr. 22, 1993

Related U.S. Application Data

[63] Continuation of application No. 07/511,651, Apr. 20, 1990, abandoned.

[51] Int. Cl.[7] .............................. C12Q 1/68; C12P 19/34; C07K 13/00
[52] U.S. Cl. .............................. 435/6; 435/91.2; 435/810; 530/350; 935/77; 935/78
[58] Field of Search .............................. 435/6, 91.2, 810; 536/22.1; 530/350; 935/77, 78

[56] References Cited

U.S. PATENT DOCUMENTS

| | | | |
|---|---|---|---|
| 4,724,202 | 2/1988 | Dattagupta et al. | 435/6 |
| 4,766,062 | 8/1988 | Diamond et al. | 435/6 |
| 4,775,619 | 10/1988 | Urdea | 435/6 |
| 4,777,129 | 10/1988 | Dattagupta et al. | 435/6 |
| 4,851,331 | 7/1989 | Vary et al. | 435/6 |
| 4,868,104 | 9/1989 | Kurn et al. | 435/6 |
| 5,185,243 | 2/1993 | Ullman et al. | 435/6 |

FOREIGN PATENT DOCUMENTS

| | | | |
|---|---|---|---|
| 0 147 665 A1 | 7/1985 | European Pat. Off. | |
| 0 185 494 A3 | 6/1986 | European Pat. Off. | |
| 0 192 168 A2 | 8/1986 | European Pat. Off. | |
| 0246864 | 11/1987 | European Pat. Off. | 435/6 |
| 0 357 336 A3 | 3/1990 | European Pat. Off. | |
| 2125964 | 3/1984 | United Kingdom . | |
| WO 87/03622 | 6/1987 | WIPO . | |
| WO 89/12696 | 12/1989 | WIPO . | |

OTHER PUBLICATIONS

Kemp et al., "Colorimetric detection of specific DNA segments amplified by polymerase chain reactions," Proc. Natl. Acad. Science USA, vol. 86, pp. 2423–2427, Apr. 1989.

*Primary Examiner*—Stephanie Zitomer
*Attorney, Agent, or Firm*—Theodore J. Leitereg

[57] ABSTRACT

A method for the detection of a polynucleotide target sequence is described. The method involves the formation of a covalent or non-covalent bonded pair of nucleotide sequences formed in response to a target polynucleotide sequence, adding nucleotide sequence specific binding proteins each capable of binding one member of the pair of nucleotide sequences, and detecting the specific binding proteins complexed to the pair of nucleotide sequences.

17 Claims, 5 Drawing Sheets

A = Target polynucleotide sequence
B = 1st Ligand
C = 2nd Ligand
D = 1st Specific nucleotide sequence ⎫ Represent bonded pair
E = 2nd Specific nucleotide sequence ⎭ of polynucleotide sequences A = Target polynucleotide sequence
B = 1st Ligand
C = 2nd Ligand
D = 1st Specific nucleotide sequence ⎫ Represent bonded pair
E = 2nd Specific nucleotide sequence ⎭ of polynucleotide sequences A = Target polynucleotide sequence
B = 1st Ligand
C = 2nd Ligand
D = 1st Specific nucleotide sequence ⎫ Represent bonded pair
E = 2nd Specific nucleotide sequence ⎭ of polynucleotide sequences
F = Covalent bond or bridge A = Target polynucleotide sequence
B = 1st Specific polynucleotide sequence
C = 2nd Specific polynucleotide sequence
D = 2nd Ligand TDPNP = Template-dependent polynucleotide polymerase
d x TPs = Nucleoside triphosphates

** = Blocked so as to disallow extension

A = Rabbit anti-mouse antibody
B = Anti ß-galactosidase antibody
C = ß-galactosidase - lac repressor fusion protein
D = Target nucleotide sequence
tet = Tet repressor protein dimer
$tet_R$ = Tet operator DNA sequence Detection

| | | |
|---|---|---|
| I.–IV. | = | Alternate methods of binding <u>tet</u> repressor protein to microtiter wells |
| O | = | <u>tet</u> repressor protein dimer |
| O | = | covalently attached <u>tet</u> repressor protein |
| O-B | = | <u>tet</u> repressor protein bound to biotin |
| A | = | avidin |
| O~H | = | <u>tet</u> repressor protein bound to hapten |
|  | = | immobilized antibody to hapten |

6,093,537

DOUBLE RECEPTOR POLYNUCLEOTIDE ASSAY METHOD

This is a Continuation of application Ser. No. 07/511,651, filed Apr. 20, 1990, now abandoned.

FIELD OF THE INVENTION

This invention relates to methods for determining the presence of polynucleotides such as a target polynucleotide sequence in a sample and compositions and kits relating thereto.

BACKGROUND OF THE INVENTION

Methods have been described for causing two nucleic acid strands to become associated as a result of the presence of a target polynucleotide. These methods are based on forming a noncovalent sandwich involving the target and two probes, each binding to a different site on the target. If the probes are contiguous or separated by one nucleotide, they can be joined in a covalent sandwich by a ligase (Goffin, C. et.al. Nucleic Acids Res. 15(21): 8755 (1987)). The ligated probe can then be amplified using known technology (Saiki, et al., Science 230:1350 (1986)). Regardless of whether the probes are ligated or amplified, provided they are covalently or non-covalently bound, the close association of the two probes can be detected by such known methods as enzyme channeling, fluorescence energy transfer and the like.

Various hybridization methods have been used in order to detect nucleic acid sequences. European Patent Application 0,192,168 describes a solution phase dual hybridization assay for the detection of polynucleotide sequences. The method described uses a separation probe which carries a reactive site capable of forming a stable covalent or non-covalent bond with a reaction partner. In the preferred practice of the invention, the reaction partner is attached to a solid support by covalent or non-covalent bonds.

World Patent Application 87/03622 describes a hybridization assay which results in high levels of amplification. Amplification is achieved by taking a primary probe, a small segment of which is hybridized to the target DNA of interest and introducing a second probe which recognizes a separate segment of the target. Using the dual probe system, increased amplification occurs upon the hybridization event taking place.

U.S. Pat. No. 4,775,619 describes a method for the detection of a specific sequence using a hybridization technique such that duplexing of the sample DNA and a probe affects the ability to modify the spatial relationship between a label and a support. The presence of the specific sequence, the target polynucleotide, is determined by the amount of label released into the medium.

U.S. Pat. No. 4,766,062 describes a method for determining the presence of a target polynucleotide in a sample wherein the probe polynucleotide complex is capable of base pair binding such that the target polynucleotide binds to the probe with a displacement of the labeled polynucleotide from the complex. In order for the detection system to be successful there must be sufficient base-pair binding to the target system in order to generate the release of a detectable signal.

Yet another method for the detection of nucleic acid hybridization is described in U.S. Pat. No. 4,724,202. The patent describes a method of detection in which the known sample or separation probe is immobilized on a solid support and contacted with a mixture containing the unknown and a labeled detection probe. The labeled detection probe is created without the use of radioactivity and without chemical modification by having a single-stranded portion of nucleic acid capable of hybridizing with the unknown connected with a non-hybridizable single or double stranded nucleic acid portion. The non-hybridizable portion includes a recognition site for a particular protein.

A method for detecting the presence of a target nucleotide sequence in a polynucleotide which comprises hybridizing a first nucleotide sequence and a second nucleotide sequence to non-contiguous portions of a target nucleotide sequence and detecting the presence of such first and second nucleotide sequences is set forth in U.S. patent application Ser. No. 07/236,967, now issued as U.S. Pat. No. 5,185,243, the disclosure of which is incorporated herein by reference.

None of the cited background art, however, provide a solution to the problem of detection of nucleic acids as described by the present invention. Using the methods of the present invention, a target polynucleotide sequence can be detected using the solution phase hybridization protocol which may be easily adapted to large scale immunochemical analysis. The methods described in the present invention can be easily applied to the design of diagnostic test systems.

SUMMARY OF THE INVENTION

One embodiment of the invention is a method for detecting a target polynucleotide sequence which method comprises: (a) forming in response to a target polynucleotide sequence a covalently or noncovalently bonded pair of nucleotide sequences for a portion of each of which exist a nucleotide sequence specific binding protein (NSSBP); and (b) detecting the NSSBPs complexed to the bonded pair of nucleotide sequences.

Another embodiment of the invention describes a method for detecting a target polynucleotide sequence in a medium suspected of containing the target polynucleotide sequence. The method comprises: (a) hybridizing to the 3' end of the target polynucleotide sequence a first ligand bound to the 3' end of a first specific nucleotide sequence wherein the specific nucleotide sequence is single stranded; (b) extending the target polynucleotide sequence by means of a template dependent polynucleotide polymerase and nucleoside triphosphates along the single stranded first specific nucleotide sequence thereby forming a double stranded first specific nucleotide sequence; (c) combining with the double stranded first specific nucleotide sequence, if not already combined, a second ligand bound to a second specific nucleotide sequence, the NSSBPs capable of binding the double stranded first and second specific nucleotide sequences; and (d) detecting the complex of the NSSBPs with a bound pair of double stranded first and second specific nucleotide sequences.

In another embodiment of the invention a method for detecting a target polynucleotide sequence in a sample is described which comprises: (a) providing in combination in a liquid medium a first ligand having a sequence hybridizable with a first portion of the target polynucleotide sequence and bound to a first specific nucleotide sequence, and a second ligand having a sequence hybridizable with a second portion of the target sequence and bound to a second specific nucleotide sequence; (b) providing means for linking the first and second ligands as a function of the presence of the target sequence; (c) combining with the linked first and second ligands, first and second NSSBPs capable of binding respectively to the first and second specific binding sequences; and (d) detecting binding between the linked NSSBPs, the detection thereof indicating the presence of the target polynucleotide sequence in the sample.

In another embodiment of the invention is described a method for detecting a bonded pair of polynucleotide sequences comprising the detection of binding of NSSBPs to two specific nucleotide sequences that comprise separate portions of the bonded pair of polynucleotide sequences.

In still another embodiment of the invention a method for performing an assay for a bonded pair of polynucleotide sequences comprised of first and second specific nucleotide sequences in a sample suspected of containing the bonded pair is described. The method comprises: (a) combining in a liquid medium (1) the sample, (2) first and second NSSBPs capable of binding, respectively, to the first and second specific nucleotide sequences wherein the first NSSBP is bound or capable of binding to a surface and the second NSSBP is bound to or capable of binding to a detectable label, and (3) the surface; (b) separating the medium from the surface; (c) combining the surface with a detectable label capable of binding the second NSSBP, when the second NSSBP is not already bound to a label; and (d) detecting the label bound to the surface.

Another embodiment of the invention describes a composition comprising a target polynucleotide bound to specific nucleotide sequences each bound to its respective NSSBP wherein one of the NSSBPs is bound to or is capable of binding to a surface and the other NSSBP is bound to or is capable of binding to a label.

In another embodiment of the invention is described a kit for use in determining a target nucleotide sequence which comprises in packaged combination (1) a pair of nucleotide sequences for a portion of each of which exists a different NSSBP, and (2) the different nucleotide specific binding proteins.

DETAILED DESCRIPTION OF THE INVENTION

Definitions

Figure 1:
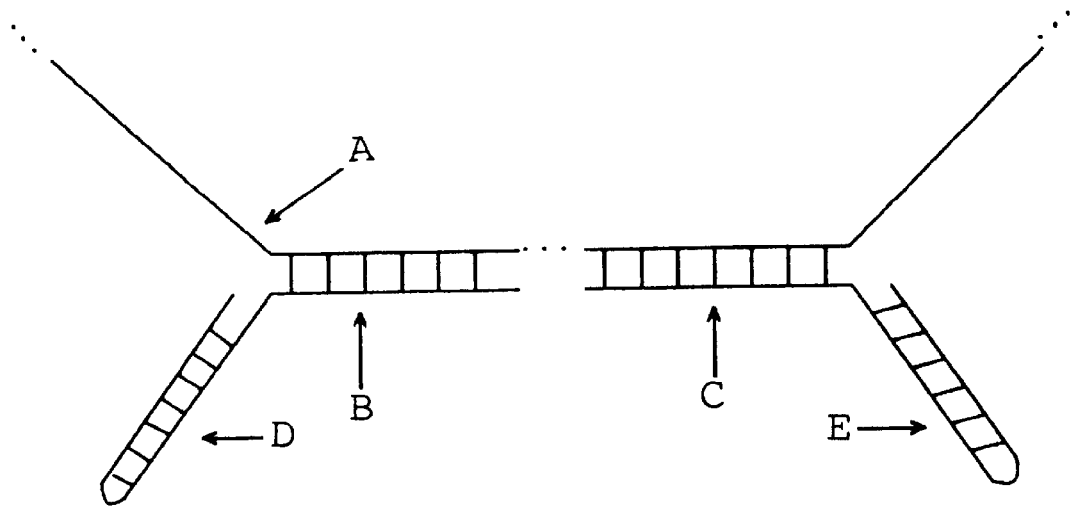
FIG. 1: Detection of a target polynucleotide sequence by hybridization of the target polynucleotide sequence with a pre-formed double stranded 1st and 2nd specific nucleotide sequence.

As set forth below, and for convenience in describing this invention, the following terms are defined as follows:

"Target polynucleotide sequences" shall mean all or a portion of a sequence of nucleotides to be identified, the identity of which is known to a sufficient extent so as to allow the preparation of a binding polynucleotide sequence that is complementary to and will hybridize with such target polynucleotide sequence. The target polynucleotide sequence usually will contain from about 12 to 1000 or more nucleotides, preferably 15 to 50 nucleotides. The target polynucleotides sequence may or may not be a portion of a larger molecule.

"Bonded pair of polynucleotide sequences" shall mean a first and a second polynucleotide sequence which become bonded together as a result of the presence of the target polynucleotide sequence. The bonding of the first and second polynucleotide sequences to form the bonded pair can be covalent or non-covalent.

"First ligand" shall mean a portion of a first polynucleotide sequence that is capable of hybridizing with the target nucleotide sequence by virtue of having a polynucleotide sequence complementary to a region of the target nucleotide sequence such that the first ligand will become bound to such region of the target nucleotide.

"Second ligand" shall mean a portion of a second polynucleotide sequence that is capable of hybridizing with the target nucleotide sequence at a region other than that of the first ligand.

"Ligation" shall mean the covalent attachment between the first and second nucleotide sequence. The chemical bonds are formed when the sequences are bound to the target polynucleotide sequence. Covalent attachment can be achieved enzymatically, as in a ligation catalyzed by T4 DNA ligase or *E. coli* DNA ligase in the presence of the necessary cofactors, or chemically.

One means for chemically forming the covalent attachment between the first and second nucleotide sequences is by use of a photoreaction. For example, one of the contiguous nucleotides can be treated to form an aryl azide and then the material can be irradiated to result in a covalent bond formation between the contiguous nucleotides.

Another means for achieving the covalent attachment of the first and second nucleotide sequences when the sequences are hybridized to non-contiguous portions of the target nucleotide sequence involves the use of a nucleotide sequence that is sufficiently complementary to the non-contiguous portion of the target nucleotide sequence lying between the first and second nucleotide sequences. For purposes of this description such a nucleotide sequence will be referred to as an intervening linker sequence. The linker sequence can be hybridized to the target sequence between the first and second nucleotide sequences. The linker sequence can then be covalently attached to both the first and second nucleotide sequence utilizing enzymatic or chemical means as referred to above. It is also possible to utilize combinations of linker sequences and polymerase to achieve a contiguous relationship between the first and second nucleotide sequences when these sequences are bound to the target nucleotide sequence.

Another means for covalently attaching the first and second nucleotide sequences when the sequences are hybridized to the target nucleotide sequence in a non-contiguous relationship involves chain extension of the second nucleotide sequence followed by carbodiimide coupling of the two sequences as described by Dolinnaya, et al. (1988). *Nucleic Acids Research,* 16 (9): 3721–3938.

"Specific nucleotide sequences" shall mean portions of the first nd second polynucleotide sequences that are bonded to and may include a portion of the first and second ligands and are capable of binding to nucleotide sequence specific binding proteins, or can become capable of binding to nucleotide sequence specific binding proteins when hybridized to a complementary polynucleotide sequence.

"Nucleotide sequences specific binding proteins (NSSBP)" shall mean proteins which recognize and are capable of binding specifically to the specific nucleotide sequences. Preferred pairs of NSSBPs and specific nucleotide sequences are, for example, repressors and operators, such as the tetracycline (tet) repressor, β-galactosidase (lac repressor), and the tryptophan (trp) repressor and their corresponding double-stranded DNA operator sequences. In addition, the lambda specific repressor protein, CRO, and the catabolite activator protein, CAP, may be used.

"Operators" shall means specific nucleotide sequences that bind repressor proteins. Operators are generally found adjacent to structural genes coding for enzymes and other proteins employed in cell metabolism and cell structure. The structural and regulatory genes that are involved in a particular cell function and are clustered together on the genetic map constitute a coordinate set of genes designated an operon. Control over transcription is dependent upon repressor proteins that interact with the operator immediately adjacent the genes coding for enzymes and other proteins needed for metabolism.

"Repressors" shall mean proteins which interact and bind to the operators. A repressor is specific for its own operator, and different operators are bound by different repressors. Examples of operator-repressor systems include lac, trp, CRO, tet and the like.

"Signal Producing System" shall consist of one or more components, at least one component being a label or reporter group. The signal producing system generates a signal that relates to the presence or amount of target polynucleotide in a sample. The signal producing system includes all of the reagents required to produce a measurable signal. The operation of the signal producing system is to produce a detectable signal related to the presence or amount of target polynucleotide in the sample.

"Non-contiguous binding" shall describe the binding wherein the first and second ligand are hybridized to the target polynucleotide sequence in a manner whereby the 3' terminal base of either the first or second ligand and the 5' terminal base of the other of said ligands are not hybridized to adjacent bases of the target polynucleotide sequence.

"Nucleoside triphosphates" shall describe a nucleoside having a 5' triphosphate substituent, usually a deoxynucleoside triphosphate. The nucleosides are pentose sugar derivatives of nitrogenous bases of either purine or pyrimidine derivation, covalently bonded to the 1'-carbon of the pentose sugar. The purine bases include adenine(A), guanine(G), and derivatives and analogs thereof. The pyrimidine bases include cytosine (C), thymine (T), uracil (U), and derivatives and analogs thereof.

"Template-dependent polynucleotide polymerase" shall means a catalyst, usually an enzyme, for forming an extension of the primary polynucleotide sequence or the target polynucleotide sequence, as the case may be, along the single stranded pattern polynucleotide where the extension is complementary to the template sequence. The template-dependent polynucleotide polymerase utilizes the nucleoside triphosphates as the building blocks for the extension which proceeds in a 5' to 3' (3' to 5' with respect to the template) direction until extension terminates. Usually, the catalysts are enzymes, such as RNA polymerases, preferably DNA polymerases such as, for example, prokaryotic DNA polymerase (I, II, or III), T4 DNA polymerase, T7 DNA polymerase, Klenow fragment, reverse transcriptase, RNA replicases, and the like derived from any source such as cells, bacteria, such as *E. coli*, plants, animals, virus, thermophilic bacteria, and so forth.

Particular Embodiments

Figure 2:
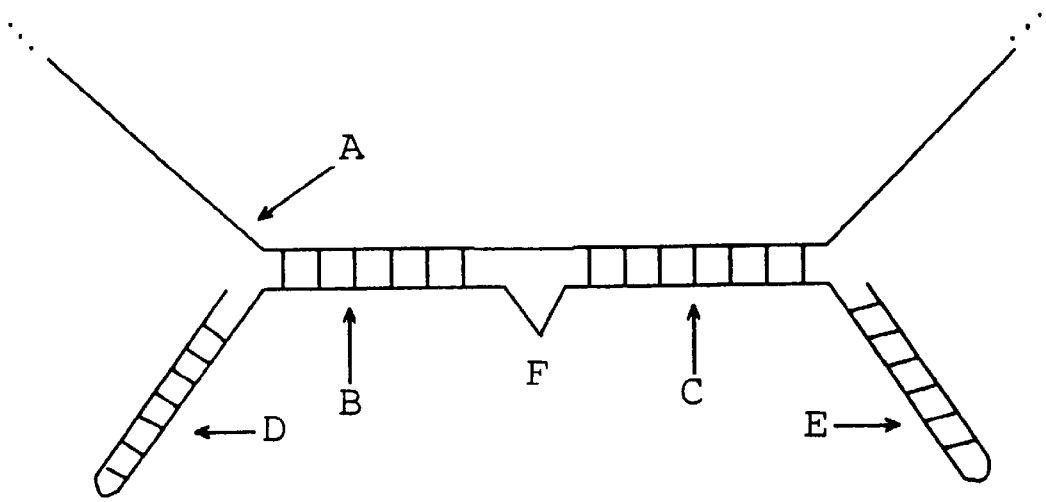
FIG. 2: Detection of a target polynucleotide sequence by covalent attachment, either chemical or enzymatic, of a 1st and 2nd specific nucleotide sequence to the target polynucleotide sequence.

One embodiment of the present invention regards a general method for determining if two probe polynucleotide sequences have become linked as a function of the presence of a target polynucleotide sequence. In such a method, a portion of a first polynucleotide sequence is a ligand for a target polynucleotide sequence and a portion of a second polynucleotide sequence is a different ligand for a different portion of the target polynucleotide sequence. Additionally, the first and second polynucleotide sequences each have different specific nucleotide sequences. Usually the ligand sequences will be single stranded. The first and second polynucleotide sequences form a bonded pair of polynucleotide sequences upon binding to different portions of the same target polynucleotide sequence. The bonding can be covalent or non-covalent. Covalent bonding can be achieved by causing the two polynucleotide sequences to both bind to the target polynucleotide sequence with subsequent target dependent ligation of the polynucleotide sequences to one another. An example of a bonded pair of polynucleotide sequences produced in this embodiment is illustrated in FIG. 1 and FIG. 2. Non-covalent bonding is achieved through base pairing.

Preferred pairs of NSSBPs and specific nucleotide sequences are repressors and operators, such as the tetracycline (tet) repressor, β-galactosidase (lac repressor), and the tryptophan (trp) repressor and their corresponding double-stranded DNA operator sequences. In addition, the lambda specific repressor protein, CRO, and the catabolite activator protein, CAP, may be used. Alternatively, restriction enzymes and the corresponding restriction sites can be used under conditions where the nuclease activity of the enzyme is suppressed.

In one aspect of the invention, one NSSBP is bound to a surface and the other NSSBP is bound to a label selected to provide a detectable event when a bonded pair of polynucleotide sequences is present. For example, each NSSBP can be on the surface of a separate set of particles where co-aggregation of the two sets provides a detectable signal that differs from self-aggregation or no aggregation of the sets of particles.

In another aspect of the invention, the bonded pair of polynucleotide sequences can be detected by pairs of interactive labels, one bound to each NSSBP, such as, for example, a fluorescer or chemiluminescer and an energy acceptor; two enzymes capable of channeling, i.e., the product of one acts as the substrate of the other; an enzyme and a polycation or polyanion capable of changing the microscopic pH and affecting enzyme activity; a particle and a polycation or anion capable of causing particle agglutination, and the like. Binding of the labels to the NSSBP may be covalent or noncovalent and where noncovalent, may involve ligand-receptor binding pairs, such as antibody-antigen, biotin-avidin, DNA hybridization, and the like.

Figure 3:
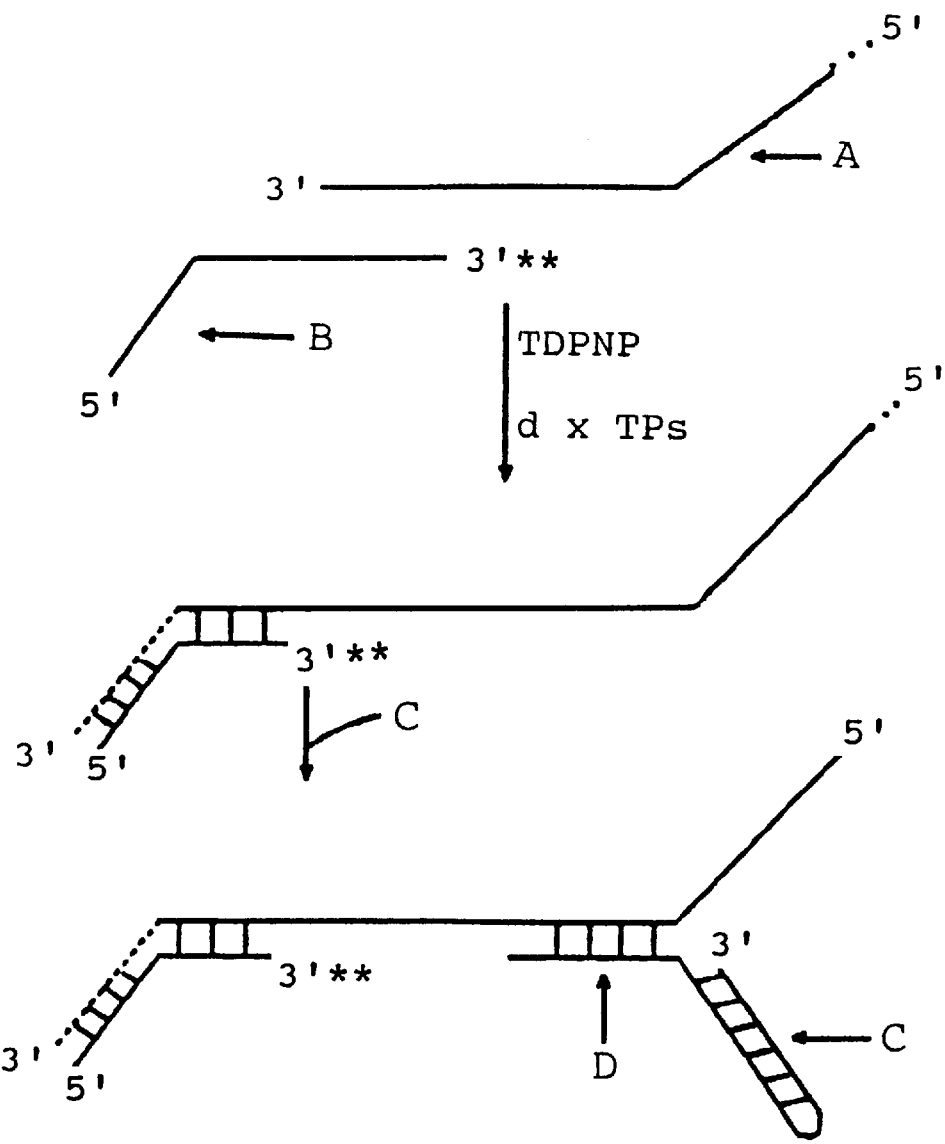
FIG. 3: Detection of a target nucleotide sequence by extension down one side of a 1st specific polynucleotide sequence.

In another application of the present invention (FIG. 3), binding of a NSSBP to a specific nucleotide sequence can occur only when the sequence is double stranded. The first and second polynucleotide sequences are capable of binding the target polynucleotide sequence. The first polynucleotide sequence is single stranded and is composed of a first ligand that is bound to the 3' end of the first specific nucleotide sequence and is capable of hybridizing with the 3' end of the target polynucleotide sequence. After causing at least the first polynucleotide sequence to hybridize with the target sequence, polynucleotide dependent nucleotide polymerase and nucleoside triphosphates are added to cause chain extension of the target sequence along the first polynucleotide sequence to form a double stranded specific nucleotide sequence. The second polynucleotide sequence is then caused to hybridize with the target sequence, if not carried out previously, thereby forming a bonded pair of polynucleotide sequences. NSSBPs capable of specifically binding the specific nucleotide sequences in the bonded pair are then added and detection of simultaneous binding to the bonded pair is carried out as described above.

Generally, a combination is provided in a liquid medium comprising a sample suspected of containing a target polynucleotide sequence, a first polynucleotide sequence complementary to a first portion of the target polynucleotide sequence, a second polynucleotide sequence complementary to a potion of the target polynucleotide sequence other than the first portion and means for hybridizing the first and second sequences with the target polynucleotide sequence.

The order of combining of the various reagents to form the combination may vary and can be simultaneous or wholly or partially sequential. Generally, a sample containing a target polynucleotide sequence is obtained. This may be combined with a pre-prepared combination of first and second nucleotide sequences, nucleoside triphosphates, and polynucleotide polymerase. Following these additions a ligase or other means to produce ligation can optionally be employed. Simultaneous addition of the above, as well as other step-wise or sequential orders of addition, may be employed. The concentration and order of addition of reagents and conditions for the method are governed generally by the desire to optimize hybridization of all the first and second nucleotide sequences with the target nucleotide sequence.

In carrying out the method of the invention an aqueous medium will be employed. The pH for the medium will usually be in the range of about 4.5 to 9.5, more usually in the range of about 5.5–8.5, and preferably in the range of about 6–8. The pH and temperature are chosen and varied, as the case may be, so as to provide for either simultaneous or sequential hybridization of the target sequence with the first and second polynucleotide sequences or extension of the first and second polynucleotide sequence along the target polynucleotide sequence. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method and desirably constant temperatures during the period for conducting the method. The temperatures for the method will generally range from about 20 to 90° C., more usually from about 30 to 70° C. preferably 37 to 50° C. However, the temperature can be varied depending on whether the above steps are carried out sequentially or simultaneously. For example, relatively low temperatures of from about 20 to 40° C. can be employed for the chain extension step, while denaturation and hybridization can be carried out at a temperature of from about 40 to 80° C.

The time period for carrying out the method of the invention will generally be long enough to achieve attachment between the first and second polynucleotide sequences, when these sequences are attached to the target polynucleotide sequence and determining whether such attachment has occurred. Generally, the time period for conducting the method will be from about 5 to 200 min. As a matter of convenience, it will usually be desirable to minimize the time period.

The concentration of the target polynucleotide sequence to be determined can be as low as $10^{-21}$M in a sample but will generally vary from about $10^{-14}$M to $10^{-19}$M, more usually from about $10^{-16}$ to $10^{-19}$M. The concentration of the first and second polynucleotide sequence and the deoxynucleoside triphosphates in the medium can vary widely. Preferably, these reagents will be present in large molar excess over the amount of target polynucleotide sequence expected. The deoxynucleoside triphosphates will usually be present in $10^{-6}$ to $10^{-2}$M, preferably $10^{-5}$ to $10^{-3}$M. The second polynucleotide sequences, as well as the first polynucleotide sequence, will usually be present in at least $10^{-12}$M, preferably $10^{-10}$M, more preferably at least about $10^{-8}$M.

The concentration of the polymerase and any cofactors in the medium can also vary substantially. These reagents may be present in as low as $10^{-12}$M but may be present in a concentration of the first and second polynucleotide sequences, the primary limiting factor being the cost of the reagents, which are usually enzymes. The final concentration of each of the reagents will normally be determined empirically to optimize the present method with respect to both speed and sensitivity.

When used together with target mediated ligation and single primer amplification, the methods of the present invention provide a homogeneous DNA assay procedure. In general, the assay procedure consists of mixing together sample containing the target nucleotide sequence under conditions which cause complexation of the probes with the target. A ligase is added to cause linking of probes to bound target. Nucleoside triphosphates are added together with a primer containing the complementary sequence at its 3' end and a nucleotide polymerase. Conditions are provided to cause amplification of the ligated sequence, which comprises the first ligand and second ligand bonded at their 5' and 3' ends, respectively. (See, for example, U.S. Ser. No. 07/236,967 incorporated herein by reference.)

In one application of the present invention, protein receptors capable of binding to the first ligand and the second ligand, usually when complexed with a complementary sequence, are combined where the first and second ligands are labeled according to any of the above methods that allow homogeneous detection, e.g., fluorescent beads and carbon particles, enzymes that can channel, and the like.

The signal associated with binding to the first and second specific nucleotide sequence is detected without separation from the assay medium. Detection of the signal will depend upon the nature of the signal producing system utilized. If the label or reporter group is an enzyme, additional members of the signal producing system would include enzyme substrates ans so forth. The product of the enzyme reaction is preferably a dye that can be detected spectrophotometrically. If the label is a fluorescent molecule the medium can be irradiated and the fluorescence determined. Where the label is a radioactive group, the medium can be counted to determine the radioactive count.

The reagents employed in the present invention can be provided in a kit in packaged combination with predetermined amounts of reagents for use in the present method in assaying for a target polynucleotide sequence present in a sample. For example, a kit useful in the present method can comprise in packaged combination with other reagents, first and second polynucleotide sequences and the corresponding nucleotide sequence specific binding proteins. The kit can further include in the packaged combination nucleoside triphosphates such as deoxynucleoside triphosphates, e.g., deoxyadenosine triphosphate (dATP), deoxyguanosine triphosphate (dGTP), deoxycytidine triphosphate (dCTP) and deoxythymidine triphosphate (dTTP). The kit can further include a polynucleotide polymerase and also means for covalently attaching the first and second sequences, such as a ligase.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method of assay in accordance with the present invention. Each reagent can be packaged in separate containers or some reagents can be combined in one container where reactivity and shelf life will permit.

The assay described in the present invention can be used to detect specific target polynucleotide sequences comprising a portion of the sample of interest. The sample of interest may be used directly where the target polynucleotide is single stranded or may be treated to denature double stranded target sequences and optionally cleave the target to obtain a fragment that contains a target polynucleotide sequence. The sample can be cleaved by known techniques such as treatment with a restriction endonuclease or other site specific chemical or enzymatic cleavage methods.

The target polynucleotide sequence may comprise a portion of, for example, nucleic acid from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The target polynucleotide sequence can be only a minor fraction of a complex mixture such as a biological sample. The target polynucleotide sequence can be obtained from various biological material by procedures well known in the art. Some examples of such biological material by way of illustration and not limitation are disclosed in Table I below.

TABLE I

Microorganisms of interest include:

Corynebacteria

*Corynebacterium diptheria*
Pneumococci

*Diplococcus pneumoniae*
Streptococci

*Streptococcus pyrogenes*
*Streptococcus salivarus*
Staphylococci

*Staphylococcus aureus*
*Staphylococcus albus*
Neisseriae

*Neisseria meningitidis*
*Neisseria gonorrhea*
Enterobacteriaciae

*Escherichia coli*
*Aerobacter aerogenes*         The colliform
*Klebsiella pneumoniae*        bacteria
*Salmonella typhosa*
*Salmonella choleraesuis*      The Salmonellae
*Salmonella typhimurium*
*Shigellae dysenteria*
*Shigellae schmitzii*
*Shigellae arabinotarda*
                               The Shigellae
*Shigellae flexneri*
*Shigellae boydii*
*Shigellae sonnei*
Other enteric bacilli

*Proteus vulgaris*
*Proteus mirabilis*            Proteus species
*Proteus morgani*
*Pseudomonas aeruginosa*
*Alcaligenes faecalis*
*Vibrio cholerae*
Hemophilus-Bordetella group                    *Rhizopus oryzae*

*Hemophilus influenza, H. ducryi*              *Rhizopus arrhizua* Phycomycetes
*Hemophilus hemophilus*                        *Rhizopus nigricans*
*Hemophilus aegypticus*                        *Sporotrichum schenkii*
*Hemophilus parainfluenzae*                    *Flonsecaea pedrosoi*
*Bordetella pertussis*                         *Fonsecaea compact*
Pasteurellae                                   *Fonsecacea dermatidis*

*Pasteurella pestis*                           *Cladosporium carrioni*
*Pasteurella tulareusis*                       *Phialophora verrucosa*

TABLE I-continued

Microorganisms of interest include:

Brucellae

*Brucella melitensis*
*Brucella abortus*
*Brucella suis*
Aerobic Spore-forming Bacilli

*Bacillus anthracis*
*Bacillus subtilis*
*Bacillus megaterium*
*Bacillus cereus*
Anaerobic Spore-forming Bacilli

*Clostridium botulinum*
*Clostridium tetani*

*Clostridium perfringens*
*Clostridium novyi*

*Clostridium septicum*
*Clostridium histolyticum*
*Clostridium tertium*
*Clostridium bifermentans*
*Clostridium sporogenes*
Mycobacteria

*Mycobacterium tuberculosis hominis*
*Mycobacterium bovis*
*Mycobacterium avium*
*Mycobacterium leprae*
*Mycobacterium paratuberculosis*
Actinomycetes (fungus-like bacteria)

*Actinomyces Isaeli*
*Actinomyces bovis*
*Actinomyces naeslundii*
*Nocardia asteroides*
*Nocardia brasiliensis*

The Spirochetes

*Treponema pallidum   Spirillum minus*
*Treponema pertenue   Streptobacillus*
                     *monoiliformis*
*Treponema carateum*
*Borrelia recurrents*
*Leptospira icterohemorrhagiae*
*Leptospira canicola*
Trypanasomes Mycoplasmas

*Mycoplasma pneumoniae*
Other pathogens

Eastern Equine Eucephalitis Virus
Listeria monocytogenes
Western Equine Eucephalitis Virus
*Erysipelothrix rhusiopathiae*
Sindbis Virus
*Streptobacillus moniliformis*
Chikugunya Virus
*Donvania granulomatis*
Semliki Forest Virus
*Bartonella bacilliformis*
Mayora Virus
Rickettsiae (bacteria-like parasites)

St. Louis Encephalitis Virus
*Rickettsia prowazekii*
California Encephalitis Virus
*Rickettsia mooseri*
Colorado Tick Fever Virus
*Rickettsia rickettsii*
Yellow Fever Virus
*Rickettsia conori*

*Aspergillus nidulans*

*Madurella mycetomi*
*Madurella grisea*
*Allescheria boydii*
*Phialophora jeanselmei*

*Microsporum gypsum*
*Trichophyton mentagrophytes*
*Keratinomyces ajelloi*
*Microsporum canis*
*Trichophyton rubrum*

*Microsporum adouini*
Viruses

Adenoviruses
Herpes Viruses

Herpes simplex
Varicella (Chicken pox)
Herpes Zoster (Shingles)
Virus B
Cytomegalovirus
Pox Viruses Variola (smallpox)
Vaccinia
Poxvirus bovis
Paravaccinia
Molluscum contagiosum
Picornaviruses Poliovirus
Coxsackievirus
Echoviruses
Rhinoviruses
Myxoviruses Influenza (A, B, and C)

Parainfluenza (1–4)
Mumps Virus
Newcastle Disease Virus
Measles Virus
Rinderpest Virus
Canine Distemper Virus
Respiratory Syncytial Virus
Rubella Virus Arboviruses

TABLE I-continued

Microorganisms of interest include:

Dengue Virus
*Rickettsia australis*
Reoviruses

*Rickettsia sibiricus*
Reovirus Types 1–3

Retroviruses

*Rickettsia akari*
Human Immunodeficiency Viruses (HIV)
*Rickettsia tsutsugamushi*
Human T-cell Lymphotrophic
Virus I & II (HTLV)
*Rickettsia burnetti*
Hepatitis

*Rickettsia quintana*
Hepatitis A Virus
Chlamydia (unclassifiable parasites
bacterial/viral)

Hepatitis B Virus

Hepatitis nonA-nonB Virus
Chlamydia agents (naming uncertain)

Tumor Viruses

Fungi

Rauscher Leukemia Virus
*Cryptococcus neoformans*
Gross Virus
Blastomyces dermatidis
Maloney Leukemia Virus
*Hisoplasma capsulatum*
*Coccidioides immitis*
Human Papilloma Viruses
*Paracoccidioides brasiliensis*
*Candida albicans*
*Aspergillus fumigatus*
*Mucor corymbifer (Absidia corymbifera)*

The double receptor polynucleotide assay method as described by invention provides a simple and straight forward assay method easily adaptable to a diagnostic testing system. The specific target nucleotide sequence identified using this assay method will frequently be characteristic of a particular disease state, genetic characteristic or abnormality.

EXAMPLES

The following examples are illustrative, and not limiting of the invention. General conditions for nucleic acid hybridization and the use of DNA and RNA modifying enzymes can be found in *Molecular Cloning: A Laboratory Manual* by Sambrook, Fritsch and Maniatis, 2nd Edition, Cold Spring Harbor Laboratory Press (1989).

Unless otherwise described, the following materials and methods for production of necessary reagents of use in carrying out the invention are known in the art and can be obtained as follows:

The lactose repressor protein may be prepared as described in the literature:

Rosenberg, J. M. et al. *Nucleic Acid Res.* 4(3):567 (1977)
Matthews, K. S., *J. Biol. Chem.* 253(12):4279 (1978)
O'Gorman, R. B. et al. *J. Biol. Chem.* 255(21):10100 (1980)
Levens, D. and P. M. Howley, *Mol. Cell. Biol.* 5(9):2307 (1985)

The presence, activity and degree of purity of the lactose repressor protein prepared using the above referenced methods can be determined using procedures described in the literature. In particular, Bourgeois, S. and A. D. Riggs, *Biochem. Biophys. Res. Comm.* 38(2):348 (1970); Barkley, M. D. and S. Bourgeois in *The Operon*, Cold Spring Harbor, N.Y. pp. 177–229 (1978); and Bourgeois, S. in *Methods in Enzymology* Vol. 21, pp. 491–500 (1971).

The tetracycline (tet) repressor protein may be prepared as described in the literature:

Hillen, W., et al. *J. Mol. Biol.* 257(11):6605 (1982)
Oehmichen, R. et al. *EMBO J.* 3(3):539 (1984)

The tet repressor protein may be assayed and characterized as described by:

Altschemied, L. and W. Hillen, *J. Mol. Biol.* 187:341 (1986)
Hillen, W. et al. *J. Mol. Biol.* 172:185 (1984)
Hillen, W. et al. *J. Mol. Biol.* 169:707 (1983)

Example 1

The presence or absence of the target DNA in a sample is determined by adding an aliquot of sample to a convenient volume of hybridization buffer, for example, 10 mM Tris (pH 7.5), 1 mM EDTA. The hybridization buffer will also contain approximately 1 mM of the first and second ligand containing nucleic acid sequences such as are shown in FIGS. 1 and 2. In one application of the example the nucleotide sequence of the D and E regions (see FIGS. 1 and 2) are those of lactose (lac) operator and tetracycline (tet) operator respectively as known from and described in the literature cited above. After denaturing any target DNA present into single strands by heating to approximately 98° C. for at least 2 minutes, the temperature of the solution is reduced so as to allow hybridization of the ligand sequence to any target nucleic acid present in the sample. The exact hybridization temperature may be calculated from the cited references considering the length of the ligand sequences to be hybridized to the target and the %AT base composition. The reaction time necessary for substantially complete hybridization will also typically be calculated from equations well known in the literature and again depending on the length of the ligand sequence and its complexity (see, for example, Albretsen, C. et al. *Anal. Biochem.* 170:193 (1988), Matthews, J. A. and Kricka, L. J. *Anal. Biochem.* 169:1 (1988), Meinkoth, J. and Wahl, G. *Anal. Biochem.* 138:267 (1984), and Miyada, C. G. and Wallace, R. B. *Methods in Enzymology*, 154:94 (1987)).

Following the formation of the ternary complex (as is shown in FIGS. 1 and 2), the solution is cooled to room temperature and a beta-galactosidase-lac repressor fusion protein (Promega Corp., Madison, Wis.), and anti-beta-galactosidase mouse monoclonal antibody (Promega Corp., Madison, Wis.), and a solid surface (such as a bead) immobilized rabbit-anti-mouse antibody (RAM bead, Bio-Rad Laboratories, Richmond Calif.) are added to the mixture. The concentration of these components and incubation time (approximately 15 minutes) will be such that all the lac operator containing nucleic acid sequence is bound onto the solid surface. The solid surface is separated from the liquid phase by centrifugation. After a washing step (an equal volume of 10 mM Tris, pH=7.5, 100 mM NaCl) and centrifugation, labeled tet repressor protein is added the tet repressor binding conditions described in the literature and referenced above. Following incubation (typically 15 minutes), removal of the unbound protein, and washing, the amount of labeled repressor material remaining above that observed with the negative control (i.e. lacking any sample or target nucleic acid) is a measure of the presence and amount of target nucleic acid present in the sample.

Figure 4:
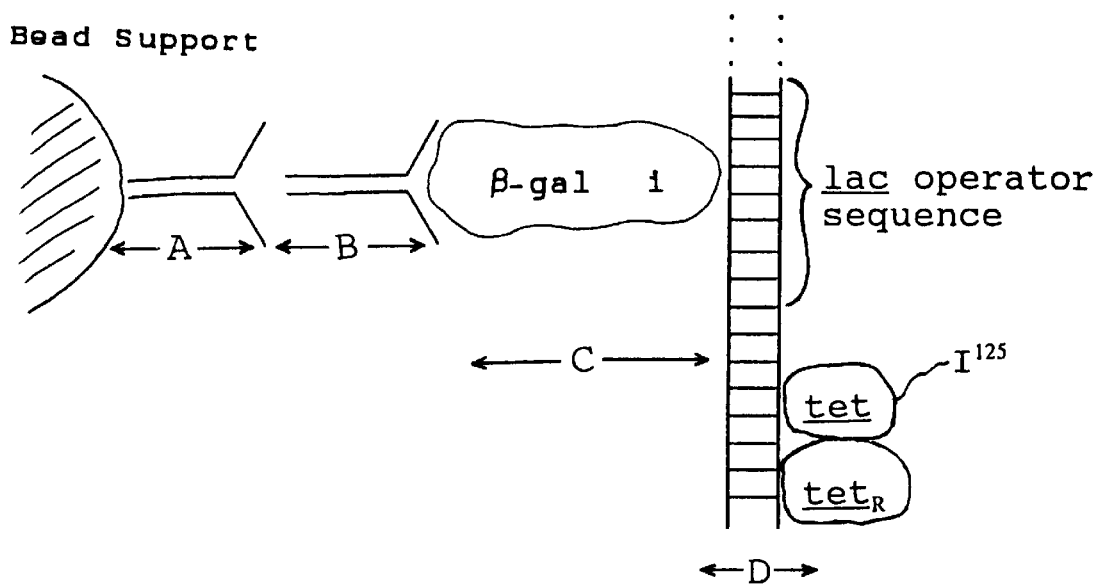
FIG. 4: Schematic of embodiment of the invention as more fully described in Example 1.

The second repressor in this example may be labeled by modification with a fluorescent dye, a radioactive marker (such as 125-Iodine), or by means of a covalently attached enzyme label turning over a detectable product when provided with its appropriate substrates in he final step of the detection reaction. The final cofiguration of this assay is shown with a model duplex DNA in FIG. 4.

Example 2

Figure 5:
FIG. 5: Schematic of embodiment of the invention as more fully described in Example 2.
Figure 5:
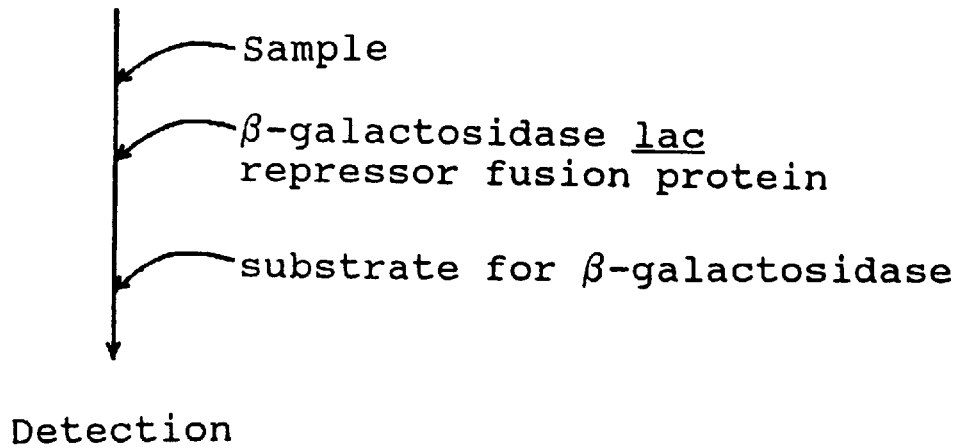
Figure 5:

An alternative method of carrying out the present invention is schematically set forth in FIG. 5. In this example, the tetracycline repressor protein is immobilized on a solid surface. This may be accomplished by passive adsorption or by the use of a covalent bond. For examples of methods for the immobilization of proteins see *Affinity Chromatography: a Practical Approach*, Dean, P. D. G. et al. eds., IRL Press, (1985), in particular, chapter 5 and the references contained therein.

In the example outlined in FIG. 5, the ternary complex produces as in Example 1 is added to the immobilized binding protein. After a suitable incubation time to allow binding (typically 15 minutes) and a washing step to remove unbound material, a second DNA binding protein, for example, the beta-galactosidate-lac repressor fusion protein is added. The second DNA binding protein is allowed to bind and washed so as to remove unbound and non-specifically bound beta-galactosidase activity. A substrate for beta-galactosidase is then added (for example "Bluo-gal", pNPG, or X-gal; BRL, Gaithersburg, Md.), and the presence of the target nucleic acid is inferred from the formation of colored dye.

The above description and examples fully disclose the invention including preferred embodiments thereof. Modifications of the methods described that are obvious to those of ordinary skill in molecular biology and related sciences are intended to be within the scope of the following claims.

What is claimed is:

1. A method for detecting the presence or absence of a target polynucleotide sequence in a sample which method comprises:
    a) combining in a medium said sample and a pair of nucleotide sequences, each nucleotide sequence of comprising a first and a second portion;
    b) hybridizing said first portion of the first nucleotide sequence with the target polynucleotide sequence and hybridizing said first portion of the second nucleotide sequence with the target polynucleotide sequence at a region different from that hybridized with the first nucleotide sequence;
    c) covalently or noncovalently attaching the hybridized first nucleotide sequence with the hybridized second nucleotide sequence to form an attached pair of nucleotide sequences;
    d) adding to said medium nucleotide sequence specific binding proteins (NSSBPs) that specifically bind the second portions of the attached pair of nucleotide sequences; and
    e) detecting the NSSBPs bound to the attached pair of nucleotide sequences, said detection indicating the presence of said target polynucleotide sequence.

2. The method of claim 1 wherein the first portions of said pair of nucleotide sequences hybridize to two non-contiguous portions of the target polynucleotide sequence.

3. The method of claim 1 wherein the regions hybridized to the first portions of said nucleotide sequences are separated by at least a single nucleotide.

4. The method of claim 1 wherein the second portions of said nucleotide sequences are different, and each second portion binds to a NSSBP selected from the group consisting of repressors, activators, restriction endonucleases, polypeptide fragments and RNA polymerases.

5. The method of claim 4 wherein the NSSBP are repressors selected from the group consisting of tetracycline (tet), lactose (lac), tryptophan (trp), CRO, CI, ara C, MMT/ARC, and lex A.

6. The method of claim 5 wherein one NSSBP is the tetracycline (tet) repressor protein or a fragment or derivative thereof.

7. The method of claim 5 wherein the first portion of one nucleotide sequence is bound to at least a portion of the tet operator and the first portion of the other nucleotide sequence is bound to at least a portion of a lac operator.

8. The method of claim 1 wherein the second portions are operators and the attached pair of nucleotide sequences is detected by the simultaneous binding of two repressors to the attached pair of nucleotide sequences.

9. The method of claim 1 wherein the attached pair of nucleotide sequences is formed by ligation of the first portions hybridized to the target polynucleotide sequence separated by at least a single nucleotide.

10. The method of claim 9 wherein the ligation is carried out by means of a ligase.

11. The method of claim 9 wherein the attached pair of nucleotide sequences is non-enzymatically ligated.

12. The method of claim 4 wherein the second portions are double stranded and the NSSBPs bind only to the double strands.

13. A method for detecting the presence or absence of a target polynucleotide sequence in a medium suspected of containing a target polynucleotide sequence comprising:
   a) hybridizing to the 3' end of the target polynucleotide sequence a first portion of a first nucleotide sequence, said first nucleotide sequence further comprising a second portion wherein the second portion is single stranded;
   b) extending the target polynucleotide sequence by means of a template dependent polynucleotide polymerase and nucleoside triphosphates along the single stranded second portion thereby forming a double stranded second portion;
   c) combining with the double stranded second portion, if not already combined, a second nucleotide sequence that covalently or noncovalently attaches to the first nucleotide sequence in the presence of said target polynucleotide sequence, comprising a first portion that hybridizes to the target polynucleotide sequence and a second double stranded portion, and nucleotide sequence specific binding proteins;
   d) binding the NSSBPs to the double stranded second portions of the hybridized first and second nucleotide sequences; and
   e) detecting the NSSBPs bound to the double stranded second portions, wherein said detection indicates the presence of said target polynucleotide sequence.

14. The method of claim 13 wherein ligation of the first portions occurs in the presence of the target polynucleotide sequence and ligase.

15. The method of claim 13 wherein the NSSBPs are selected from the group consisting of repressors, activators, restriction endonucleases, and RNA polymerases.

16. A kit for use in determining a target nucleotide sequence which comprises in packaged combination:

a pair of nucleotide sequences for a portion of each of which exists a different nucleotide sequence specific binding protein (NSSBP), and the different nucleotide sequence specific binding proteins.

17. The kit of claim 16 which further comprises a combination of nucleoside triphosphates selected from the group consisting of dATP, dGTP, dCTP and dTTP and corresponding derivatives thereof, and a polynucleotide polymerase.

* * * * *